United States Patent [19]

Harris

[11] Patent Number: 4,503,222
[45] Date of Patent: Mar. 5, 1985

[54] PESTICIDAL NITROMETHANE DERIVATIVES

[75] Inventor: Martin Harris, Sittingbourne, England

[73] Assignee: Shell Oil Company, Houston, Tex.

[21] Appl. No.: 571,405

[22] Filed: Jan. 17, 1984

[30] Foreign Application Priority Data

Jan. 20, 1983 [GB] United Kingdom ................ 8301504

[51] Int. Cl.$^3$ .......................................... C07D 417/00
[52] U.S. Cl. .................................................... 544/54
[58] Field of Search ............................. 544/54; 424/246

[56] References Cited

U.S. PATENT DOCUMENTS

| 4,033,953 | 7/1977 | Tieman | 544/54 |
| 4,044,128 | 8/1977 | Roman | 544/54 |
| 4,225,603 | 9/1980 | Tieman | 544/54 |
| 4,279,903 | 7/1981 | Anderson | 544/54 |

Primary Examiner—Glennon H. Hollrah
Assistant Examiner—D. Dinner

[57] ABSTRACT

Sulphenyl nitromethane derivatives of formula:

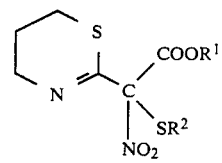

in which $R^1$ represents an alkyl group or a cycloalkylalkyl group; and $R^2$ represents an alkyl group optionally substituted by one or more halogen atoms or an aryl group optionally substituted by one or more halogen atoms or by one or more alkyl or alkoxy groups, exhibit pesticidal, in particular insecticidal activity. They are prepared by reacting the corresponding nitromethylene carboxylate with a sulphenyl halide $R^2$—S—Hal in the presence of a base.

3 Claims, No Drawings

PESTICIDAL NITROMETHANE DERIVATIVES

This invention relates to certain sulphenyl nitromethane derivatives, to a process for their preparation and to their use as pesticides, in particular as insecticides.

Accordingly the invention provides sulphenyl nitromethane derivatives of formula:

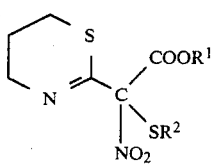

in which $R^1$ represents an alkyl group or a cycloalkyl-alkyl group; and $R^2$ represents an alkyl group optionally substituted by one or more halogen atoms, or an aryl group optionally substituted by one or more halogen atoms or by one or more alkyl or alkoxy groups.

Preferably $R^1$ represents an alkyl group of 1 to 6 carbon atoms, for example, methyl or propyl, or a cycloalkyl-alkyl group of up to 6 carbon atoms, for example, cyclopropylmethyl; and $R^2$ represents an alkyl group of 1 to 12 carbon atoms, optionally substituted by up to two chlorine atoms, for example methyl, dichloroethyl or decyl, or a phenyl group optionally substituted by one or two chlorine atoms, by a bromine atom or by an alkyl or alkoxy group of 1 to 6 carbon atoms, for example methyl or methoxy.

It will be appreciated that the sulphenyl nitromethane derivatives of formula I contain an asymmetric carbon atom and are therefore capable of existing as different optically active isomers. The invention includes both the individual isomers and mixtures of such isomers.

The invention includes also a process for the preparation of sulphenyl nitromethane derivatives of formula I, which comprises reacting a nitromethylene derivative of formula:

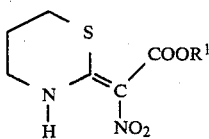

with a sulphenyl halide of formula

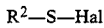

$$R^2-S-Hal \qquad III$$

in which $R^1$ and $R^2$ are as defined above in relation to formula I and Hal represents a halogen, preferably chlorine, atom, in the presence of a base. The base used is preferably an organic base such as a tertiary amine, a trialkylamine such as triethylamine being particularly preferred. The reaction is preferably carried out in an organic solvent, for example, a chlorinated hydrocarbon, such as dichloromethane, or an ether such as tetrahydrofuran. The preferred temperatures for the reaction are $-10°$ to $+10°$ C., for example 0° C.

The sulphenyl nitromethane derivatives of the invention are of interest as pesticides, particularly as insecticides. They exhibit activity against such pests as the larval "caterpillar" or "worm" forms of insects of, for example the genus Heliothis and the genus Spodoptera.

The compounds also have acceptable stability towards light and oxidation.

Accordingly the invention includes within its scope pesticidal compositions comprising a sulphenyl nitromethane derivative of the invention together with a carrier.

Such a composition may contain a single compound or a mixture of several compounds of the invention. It is also envisaged that different isomers or mixtures of isomers may have different levels or spectra of activity and thus compositions may comprise individual isomers or mixtures of isomers. The invention further provides a method of combating pests, particularly insect pests at a locus infested or liable to infestation by such pests, which comprise applying to the locus a pesticidally effective amount of a compound or composition according to the present invention.

The carrier in a composition of the invention may be a solid or a liquid, including a material which is normally gaseous but which has been compressed to form a liquid, inorganic or organic, and of synthetic or natural origin. The active ingredient is suitably formulated with at least one carrier to facilitate its application to the locus, for example plants, seeds or soil, to be treated, or to facilitate storage, transport or handling.

Preferably a composition of the invention contains at least two carriers, at least one of which is a surface-active agent. The surface-active agent may be an emulsifier, a dispersing agent or a wetting agent. It may be non-ionic or ionic. Pesticidal compositions are generally formulated and transported in a concentrated form which is subsequently diluted by the farmer or other user before application. A surface-active agent facilitates this process of dilution.

Any of the carriers commonly used in the formulation of pesticides may be used in the compositions of the invention, and suitable examples of these are to be found, for example, in British Patent Specification No. 1,232,930.

The composition of the invention may, for example, be formulated as a wettable powder, microcapsules, a dust, granules, a solution, an emulsifiable concentrate, an emulsion, a suspension concentrate or an aerosol. The composition may have conrolled release properties, or may be suitable for use as a bait.

Wettable powders usually contain 25, 50 or 75% of active ingredient and may contain, in addition to inert solid material, 3–10%w of a dispersing agent and, where necessary, 0–10%w of a stabiliser, a penetrant and/or a sticker. A dust is usually formulated as a dust concentrate having a composition similar to that of a wettable powder but without a dispersant, and is diluted in the field with further solid carrier to give a composition usually containing ½–10%w of active ingredient.

Granules usually have a size in the range of from 10 to 100 BS mesh (1.676–0.152 mm) and may be manufactured by aggolmeration or impregnation techniques. Generally, granules will contain ½–25% active ingredient and 0–10%w of additives, for example a stabiliser, slow release modifier and/or a binding agent.

Emulsifiable concentrates usually contain, in addition to a solvent, and, when necessary, co-solvent, 10–50%w/v active ingredient, 2–20%w/v emulsifier and 0–20%w/v of other additives, for example a stabiliser, a penetrant and/or a corrosion inhibitor. A suspension concentrate is a stable, nonsedimenting, flowable product and usually contains 10–75%w active ingredient, 0.5–15%w of dispersing agent, 0.1–10%w of suspending agent, for example protective colloid and/or a thixotropic agent, and 0–10%w of other additives including, for example, a defoamer, a corrosion inhibitor, a stabiliser, a penetrant and/or a sticker, and as dispersant, water or an organic liquid in which the active ingredient is substantially insoluble. Certain organic additives and/or inorganic salts may be dissolved in the dispersant to assist in preventing sedimentation or as anti-freeze for water.

The aqueous dispersions and emulsions formed by diluting a wettable powder or an emulsifiable concentrate of the invention with water, also lie within the scope of the present invention. Such dispersions and emulsions may be of the water-in-oil or of the oil-in-water type, and may have a thick "mayonnaise"-like consistency.

A composition of the invention may also contain other ingredients, for example, one or more other compounds possessing pesticidal, herbicidal or fungicidal properties, or attractants, for example pheromones or food ingredients, for use in baits and trap formulations.

The present invention is further illustrated by the following examples.

EXAMPLE 1

Methyl nitro(p-tolylsulphenyl)-(5,6-dihydro-4H-1,3-thiazin-2-yl)acetate

To a solution of methyl nitro(tetrahydro-2H-1,3-thiazin-2-ylidene) acetate (0.875 g) and triethylamine (0.62 ml) in dichloromethane (10 ml) at 0° C. under nitrogen was added dropwise over a period of 3 minutes a solution of p-tolylsulphenyl chloride (0.7 g) in dichloromethane. The reaction mixture was stirred for a further 30 minutes at 0° C. then washed with 2% hydrochloric acid followed by water. The organic phase was then dried (MgSO$_4$) and the solvent removed under reduced pressure. The residual oil was triturated with methanol to yield the required product as a white crystalline solid m.p. 85°–89° C.

Analysis calculated for $C_{14}H_{16}O_4N_2S_2$: C 49.4%;H 4.7%; N 8.2%. Found: C 49.3%;H 4.7%; N 8.2%.

EXAMPLES 2 to 20

Following procedures similar to that given in Example 1 further compounds were prepared. The melting points and analyses of these compounds are set out in Table A.

TABLE A

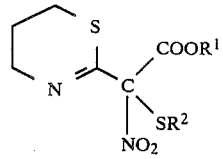

| Example No. | R$^1$ | R$^2$ | m.p. °C. | | C % | H % | N % |
|---|---|---|---|---|---|---|---|
| 2 | CH$_3$ | phenyl | 95–97 | Calc. for C$_{13}$H$_{14}$O$_4$N$_2$S$_2$ | 47.9 | 4.3 | 8.6 |
|   |   |   |   | Found | 47.8 | 4.4 | 8.6 |
| 3 | CH$_3$ | m-tolyl | 104 | Calc. for C$_{14}$H$_{16}$O$_4$N$_2$S$_2$ | 49.4 | 4.7 | 8.2 |
|   |   |   |   | Found | 49.0 | 4.6 | 8.3 |
| 4 | CH$_3$ | 4-chlorophenyl | 92–93 | Calc. for C$_{13}$H$_{13}$O$_4$N$_2$S$_2$Cl | 43.3 | 3.6 | 7.8 |
|   |   |   |   | Found | 43.2 | 3.6 | 7.8 |
| 5 | CH$_3$ | 4-bromophenyl | 91–93 | Calc. for C$_{13}$H$_{13}$O$_4$N$_2$S$_2$Br | 38.5 | 3.2 | 6.9 |
|   |   |   |   | Found | 38.2 | 3.2 | 7.0 |
| 6 | CH$_3$ | 3,4-dichlorophenyl | 124–125 | Calc. for C$_{13}$H$_{12}$O$_4$N$_2$S$_2$Cl$_2$ | 39.5 | 3.0 | 7.1 |
|   |   |   |   | Found | 39.3 | 2.8 | 7.0 |
| 7 | CH$_3$ | 4-methoxyphenyl | 114–116 | Calc. for C$_{14}$H$_{17}$O$_5$N$_2$S$_2$ | 47.2 | 4.5 | 7.9 |
|   |   |   |   | Found | 47.1 | 4.6 | 7.6 |
| 8 | CH$_3$ | n-C$_{10}$H$_{21}$ | oil | Calc. for C$_{17}$H$_{30}$O$_4$N$_2$S$_2$ | 52.3 | 7.7 | 7.2 |
|   |   |   |   | Found | 53.1 | 8.2 | 6.0 |
| 9 | CH$_3$ | CH$_3$ | oil | Calc. for C$_8$H$_{12}$O$_4$N | 36.4 | 4.6 | 10.6 |
|   |   |   |   | Found | 34.5 | 4.8 | 9.4 |
| 10 | —CH$_2$—◁ | m-tolyl | oil | Calc. for C$_{17}$H$_{20}$O$_4$N$_2$S$_2$ | 53.7 | 5.3 | 7.4 |
|   |   |   |   | Found | — | — | — |
| 11 | n-C$_3$H$_7$ | m-tolyl | oil | Calc. for C$_{16}$H$_{20}$O$_4$N$_2$S$_2$ | 52.2 | 5.4 | 7.6 |
|   |   |   |   | Found | 51.7 | 5.7 | 7.5 |
| 12 | n-C$_3$H$_7$ | 4-bromophenyl | oil | Calc. for C$_{15}$H$_{17}$O$_4$N$_2$S$_2$Br | 41.6 | 3.9 | 6.5 |
|   |   |   |   | Found | 40.0 | 3.8 | 6.2 |
| 13 | n-C$_3$H$_7$ | 4-chlorophenyl | oil | Calc. for C$_{15}$H$_{17}$O$_4$N$_2$S$_2$Cl | 46.3 | 4.4 | 7.2 |
|   |   |   |   | Found | 46.4 | 4.1 | 6.4 |
| 14 | n-C$_3$H$_7$ | p-tolyl | oil | Calc. for C$_{16}$H$_{20}$O$_4$N$_2$S$_2$ | 52.2 | 5.4 | 7.6 |
|   |   |   |   | Found | — | — | — |
| 15 | n-C$_3$H$_7$ | 3,4-dichlorophenyl | 85–86 | Calc. for C$_{15}$H$_{16}$O$_4$N$_2$S$_2$Cl$_2$ | 42.6 | 3.8 | 6.6 |
|   |   |   |   | Found | 41.8 | 3.7 | 6.5 |
| 16 | n-C$_3$H$_7$ | phenyl | oil | Calc. for C$_{15}$H$_{18}$O$_4$N$_2$S$_2$ | 50.9 | 5.1 | 7.9 |
|   |   |   |   | Found | 49.7 | 5.2 | 7.9 |
| 17 | n-C$_3$H$_7$ | CH$_3$ | oil | Calc. for C$_{10}$H$_{16}$O$_4$N$_2$S$_2$ | 41.1 | 5.5 | 9.6 |
|   |   |   |   | Found | 40.5 | 5.4 | 9.5 |
| 18 | —CH$_2$— | p-tolyl | oil | Calc. for C$_{17}$H$_{20}$O$_4$N$_2$S$_2$ | 53.7 | 5.3 | 7.4 |
|   |   |   |   | Found | 53.3 | 5.4 | 7.2 |
| 19 | CH$_3$ | —CH$_2$CHCl$_2$ | oil | Calc. for C$_9$H$_{12}$O$_4$N$_2$S$_2$Cl$_2$ | 31.1 | 3.5 | 8.1 |
|   |   |   |   | Found | 31.6 | 3.6 | 7.7 |

TABLE A-continued

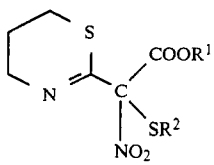

| Example No. | R¹ | R² | m.p. °C. | | Analysis C % | H % | N % |
|---|---|---|---|---|---|---|---|
| 20 | n-C₃H₇ | n-C₁₀H₂₁ | oil | Calc. for $C_{19}H_{34}O_4N_2S_2$ | 54.6 | 8.1 | 6.7 |
| | | | | Found | 55.1 | 8.5 | 6.5 |

Pesticidal Activity

The pesticidal activities of the compounds of the invention were assessed employing the following insect pests. Insect: *Spodoptera littoralis* (S.l.) *Aedes aegypti* (A.a.).

The test methods employed for each species appear below. In each test, unless otherwise stated, a 0.2% solution or suspension of each test compound in 16.7% acetone in water containing 0.04% Triton X-100 (Trade Mark) was sprayed onto the test species. Controls were sprayed with a control solution of water, acetone and Triton X-100 (Trade Mark) in the same proportions. The tests were all conducted under normal insectary conditions 23° C.±2° C. (fluctuating light and humidity).

(i) *Spodoptera littoralis*

Second instar larvae were used in the tests. Each test solution and the control solution was sprayed onto a separate petri dish containing a nutrious diet on which the *Spodoptera littoralis* larvae had been reared.

When the spray deposit had dried each dish was infested with 10 2nd instar larvae. Mortality assessments were made 1 and 7 days after spraying and the percentage mortality calculated.

(ii) *Aedes aegypti*

Early 4th instar larvae were used in the tests. Test solutions were made up to 3 ppm of active ingredient in water containing 0.04% Triton X-100 (Trade Mark). Acetone was initially present to aid solution, but was subsequently allowed to evaporate off.

Ten early 4th instar larvae were placed in 100 ml of the test solution. After 48 hours, larval mortality (as a percentage) was recorded.

Any surviving larvae were then fed with a small quantity of animal feed pellets and the final percentage mortality of adults and pupae made when all the larvae had either pupated and turned into adults, or died.

The results of these tests are shown in Table B in which the test species are identified by the initials noted above and the activity of each compound is expressed in terms of the percentage mortality:

TABLE B

| Compound of Example | S.l. 24 hr | S.l. 7 day | A.a. 24 hr | A.a. Final |
|---|---|---|---|---|
| 1 | A | A | C | C |
| 2 | A | A | C | C |
| 3 | A | A | C | B |
| 4 | C | A | B | B |
| 5 | C | A | A | A |
| 6 | C | A | A | A |
| 7 | C | A | B | A |
| 8 | C | A | B | A |
| 9 | B | B | C | C |
| 10 | B | B | C | B |
| 11 | A | A | C | B |
| 12 | A | A | B | B |
| 13 | A | A | C | A |
| 14 | A | A | C | C |
| 15 | A | A | A | A |
| 16 | C | A | C | C |
| 17 | A | A | C | C |
| 18 | B | A | C | C |
| 20 | A | A | A | A |

A denotes 90–100% mortality
B denotes 50–80% mortality
C denotes 0–40% mortality

I claim:
1. Sulphenyl nitromethane derivatives of formula:

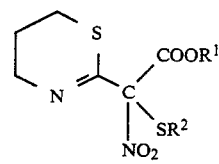

in which R¹ represents an alkyl group or a cycloalkylalkyl group of up to 6 carbon atoms and R² represents an alkyl group of 1 to 12 carbon atoms optionally substituted by one or more halogen atoms or a phenyl group optionally substituted by one or more halogen atoms or by one or more alkyl or alkoxy groups of 1 to 6 carbon atoms.

2. Sulphenyl nitromethane derivatives as claimed in claim 1 in which R² represents an alkyl group of 1 to 12 carbon atoms optionally substituted by up to two chlorine atoms, or a phenyl group optionally substituted by one or two chlorine atoms or by a bromine atom or by an alkyl or alkoxy group of 1 to 6 carbon atoms.

3. Sulphenyl nitromethane derivatives as claimed in claim 1 or 2 in which R¹ represents a methyl, propyl or cyclopropylmethyl group; and R² represents a methyl, dichloroethyl or decyl group, or a phenyl group optionally substituted by one or two chlorine atoms, by a bromine atom or by a methyl or methoxy group.

* * * * *